United States Patent

Drauz et al.

[11] Patent Number: 5,874,121
[45] Date of Patent: Feb. 23, 1999

[54] METHOD OF PRODUCING L-ASPARTYL-D-ALANINE-N-(THIETHANE-3-YL)-AMIDES

[75] Inventors: Karlheinz Drauz, Freigericht; Günter Knaup, Bruchköbel; Stefan Retzow; Michael Schwarm, both of Alzenau; Christoph Weckbecker, Hanau, all of Germany

[73] Assignee: Degussa AG, Frankfurt, Germany

[21] Appl. No.: 894,518

[22] PCT Filed: Jan. 31, 1996

[86] PCT No.: PCT/EP96/00393

§ 371 Date: Nov. 21, 1997

§ 102(e) Date: Nov. 21, 1997

[87] PCT Pub. No.: WO96/26213

PCT Pub. Date: Aug. 29, 1996

[30] Foreign Application Priority Data

Feb. 21, 1995 [DE] Germany ......... 195 05 933.6

[51] Int. Cl.$^6$ ............ C07D 103/52; C07D 103/50; C07D 307/22; C07C 87/34
[52] U.S. Cl. ............ 426/548; 426/590; 530/330
[58] Field of Search ........................ 426/548, 590; 530/330

[56] References Cited

U.S. PATENT DOCUMENTS 4,411,925 10/1983 Brennan et al. ............ 426/548

FOREIGN PATENT DOCUMENTS 394 854   7/1992   Austria .
034 876   9/1981   European Pat. Off. .

OTHER PUBLICATIONS

Chemical Abstracts, vol. 81, No. 19, Nov. 11, 1974, abstract No 121016u, Nagase et al: "Alpha–L–Asparaginyl––L–amino acid esters", p. 578; XP002003940 see abstract & JP,A,07 435 352, Apr. 1, 1974.

Chemical Abstracts, vol. 114, No. 3, Jan. 21, 1991, abstract No. 24570j. Burger et al: "Regiospecific reaction with omega–carboxy alpha–amino acids. A simple synthseis of aspartame", p. 765; XP002003941 see abstract & Chem. Zeitung, vol. 114, No. 7–8, 1990, pp. 249–251.

*Primary Examiner*—Robert J. Hill, Jr.
*Assistant Examiner*—M. Borin
*Attorney, Agent, or Firm*—Pillsbury Madison & Sutro LLP

[57] ABSTRACT

The invention concerns a method of producing L-aspartyl-D-alanine-N-(thietane-3-yl) amides of general formula I by reacting D-alanine-thietane amides of general formula II with oxazolidinone compounds of general formula III in an inert organic solvent, wherein $R^1$ stands for H or a selectively separable protective group, $R^2$–$R^5$ independently of one another, are identical or different and stand for H or linear or branched $C_1$–$C_4$-alkyl, and $R^6$ and $R^7$, independently of each other, are identical or different and stand for H, linear or branched $C_1$–$C_4$-alkyl, aryl or a group which activates the carbonyl group.

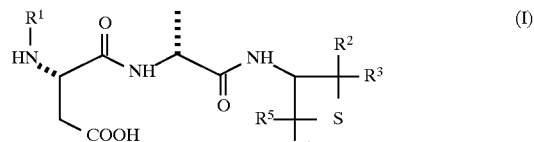

(I)

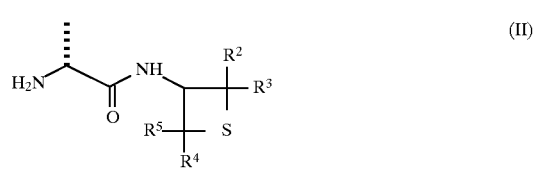

(II)

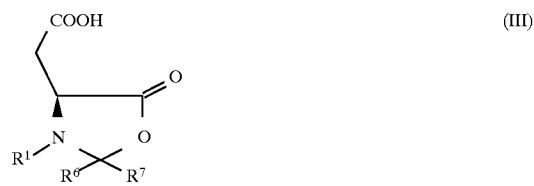

(III)

30 Claims, No Drawings

METHOD OF PRODUCING L-ASPARTYL-D-ALANINE-N-(THIETHANE-3-YL)-AMIDES

This application is the national phase of international application PCT/EP96/00393, filed Jan. 31, 1996 which was designated the U.S.

The invention is relative to a method of producing L-aspartyl-D-alanine-N-(thietane-3-yl)-amides of the general formula I

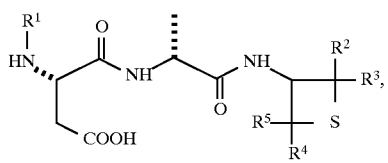

in which $R^1$ stands for H or a protective group capable of being split off and $R^2$–$R^5$ signify independently of each other and equally or differently H or $C_1$–$C_4$ alkyl, linear or branched.

Compounds with $R^1$=H are dipeptide sweeteners (U.S. Pat. No. 4,411,925; EP-A 34,876). Alitame ($R^1$=H, $R^2$–$R^5$=$CH_3$) has a sweetening strength approximately 2000 times as great as that of sugar (ACS Symp. Ser. 1992, 450, 57).

The compounds of formula I are preferably produced starting from thietane amines, D-Ala and L-Asp.

These components can basically be coupled to each other in different ways. Thus, the synthesis of compounds of general formula I is described by way of example in U.S. Pat. No. 4,411,925. However, the syntheses of the three coupling partners (thietane amine and activated/protected D-Ala and L-Asp) take place in it in a rather complicated manner in accordance with methods known in the literature. This is elucidated using the example of alitame.

2,2,4,4-tetramethyl-3-thietanone is produced from diisopropylketone after dibromination by cyclization with disodium sulfide, which 2,2,4,4-tetramethyl-3-thietanone is reduced in the ammonium acetate/sodium cyanoborohydride system in 42% yield to thietane amine. The amine can also be obtained according to EP-A 168,112 by converting 2,2,4,4-tetramethylthienanone into an oxime (<30% yield) and reduction by lithium aluminum hydride (42% yield). Furthermore, U.S. Pat. No. 4,851,548 teaches the reduction of 2,2,4,4 -tetramethyl-3-thietanone to thietane amine by means of Leuckart-Wallach reaction in a max. 65% yield.

Various strategies are indicated in U.S. Pat. No. 4,411,925 for the coupling of the three reaction partners which take place according to generally current peptide coupling methods with correspondingly many protective and de-protective steps. Thus, a relatively expensive N-benzyloxycarbonyl-L-aspartic-acid-β-benzylester which is difficult to synthesize and is reacted after activation with D-Ala-thietane amide is used for the selective α coupling of L-Asp. Another formula indicated there uses N-thiocarboxyanhydride as activated and at the same time protected L-Asp. This can be synthesized only with difficulty and in small yields (42% yield). In addition, materials which are critical as regards protection of labor and environmental impact such as methylene chloride, carbon disulfide and phosphorus tribromide are required for its synthesis.

In contrast thereto, the invention had the problem of indicating a method of producing compounds of general formula I, but especially of alitame, which signifies a considerable improvement in methodology as well as in yield and expenditure of time in over the known methods.

This problem is solved by reacting D-alanine-thietane amides of the general formula II

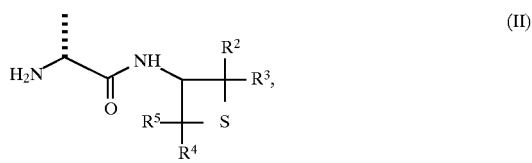

in which $R^2$–$R^5$ have the significance indicated in formula I with oxazolidinone compounds of the general formula III

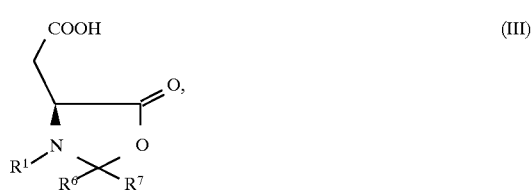

in which $R^1$ has the significance indicated in formula I and $R^6$ and $R^7$ stand independently of one another and equally or differently for H, $C_1$–$C_4$ alkyl, linear or branched, $C_1$–$C_4$ haloalkyl, linear or branched, or a preferably halogen-substituted group activating the carbonyl group in an inert organic solvent.

1,3-oxazolidin-5-ones and their fundamental suitability for peptide coupling are basically known (J. P. Greenstein, M. Winitz, Chemistry of the Amino Acids, Wiley, 1961, p. 1024; Houben-Weyl, vol. 15/I, p. 91ff).

In spite of their simple accessibility and, in the case of aspartic acid, high regioselectivity they have not been widely used previously for producing aspartic acid peptides. The reasons for this are that there was the opinion that the carbonyl compound used in excess for production and released in the reaction leads to undesired side reactions with the amine component used for coupling and therefore an expensive purification and isolation are unavoidable (Greenstein, Winitz, p. 1027, Houben-Weyl, vol. 15/II, p. 95).

Furthermore, since the amine component of formula II with the thietane ring to be used to produce compounds of formula I has another, very reactive functional group (Comprehensive Heterocyclic Chemistry, vol. 7, p. 419 ff), it was very surprising that the compounds of formula I can be produced with the method of the invention in good yields and in a simple manner.

Although oxazolidinones are suited for the production of aspartame (Chemiker-Ztg. 1990, 114, 249; U.S. Pat. No. 4,730,076; JP-A-7435352) they have nevertheless not been used previously on an industrial scale for the synthesis of aspartame, among other things for the reasons indicated above. Further reasons for this can be in part uneconomicalness (boc-oxazolidinones, oxazolidinones from hexafluoroacetone, teoc-oxazolidinones, tosyl-oxazolidinones) and, in part, lacking possibilities of splitting off the protective groups (moc-oxazolidinones).

If very reactive carbonyl components are used as oxazolidinone builders the protection of the amino function of the amino acid can be eliminated. Active carbonyl components are e.g. all aldehydes and ketones which readily form hydrates.

In an advantageous method variant of the invention a compound of formula III with $R^1$=H, $R^7$=$CF_3$ and $R^6$=$CF_3$ is used which was obtained by reacting L-aspartic acid with hexafluoroacetone.

The compound of general formula III with $R^1$=H, $R^6$ and $R^7$=$CF_3$ is bis-(2,2-trifluoro-4-carboxymethyl)-1,3-oxazolidin-5-one, which is a representative of the oxazolidinones of L-Asp with active carbonyl component.

This compound is already known (Chem. Ber. 1964, 99, 1461) and has already been used for peptide couplings. However, in the production of oxazolidinone DMSO was always used as solvent and the oxazolidinone isolated by an expensive aqueous workup. The difficultly volatile DMSO and the excess hexafluoroacetone required for bonding the reaction water are extracted thereby with water, as a result of which a recycling of the DMSO and of the hexafluoroacetone is almost excluded. It was found in a totally surprising manner that the reaction of L-Asp with hexafluoroacetone can be carried out in an especially advantageous manner in DMF as solvent and that the excess hexafluoroacetone and/or hexafluoroacetone hydrate can be completely recovered. To this end hexafluoroacetone trihydrate is introduced after dehydrogenation into a suspension of L-Asp in DMF. After the introduction of 2.5 to 3 equiv. hexafluoroacetone the mixture is agitated until all L-Asp has gone into solution. After the reaction is completed hexafluoroacetone hydrate is first removed in a vacuum and then the solvent. This renders both compounds accessible for recycling.

The desired oxazolidinone ($R^1$=H, $R^{6,7}$=$CF_3$) accumulates as colorless oil and can be used in an especially advantageous manner without further purification or isolation in the following coupling reaction.

After completed coupling with D-Ala-thietane amide, which takes place sufficiently rapidly at RT [room temperature] already and in >80% yield, the hexafluoroacetone becoming free is removed in a vacuum and also trapped. In this manner 85% of the toxic and environmentally damaging hexafluoroacetone used can be recycled. The remaining solution is concentrated by evaporation and can be worked up, as is described e.g. in U.S. Pat. No. 4,411,925.

Another representative of the oxazolidinones of L-Asp with active carbonyl component is a compound of general formula III with $R^1$=H, $R^6$=$CCl_3$ and $R^7$=H. It can be obtained within the framework of the invention by reacting L-aspartic acid with chloral.

The preparation of oxazolidinones from amino acids and chloral has already been described in Angew. Chem. 1959, 71, 339 but not the synthesis starting from L-Asp and chloral. AT 394,854 mentions oxazolidinone from Asp and chloral. However, according to this quote from the literature acyl-protected oxazolidinone is necessary for reaction with amines. It was now surprisingly found that a compound of formula III with $R^1$=H and $R^6$ or $R^7$=$CCl_3$ can be used for coupling with the D-Ala-thietane amide of general formula II without the N-function having to be protected by an acyl group and without the oxazolidinone having to be isolated. According to the invention it is best to proceed in such a manner that a suspension of L-Asp in a little DMSO is compounded with an excess of chloral, preferably 2 equiv., and agitated several hours, preferably 4 to 6 h, at RT. The solution is then compounded with an indifferent org. solvent, preferably an ether, THF is especially preferred, and agitated at temperatures below 0° C., preferably −15° C., with an excess of the amine component (general formula II). After several hours reaction time, preferably 12 hours, the matter is worked up by filtration. After column chromatographic purification the coupling product ($R^1$=H) is obtained in >80% yield.

Also, all N-acyl-, -alkyloxycarbonyl, -arylalkyloxycarbonyl- as well as heterosubstituted -alkyl- and -arylalkyloxycarbonyl-protected L-aspartic acids known from peptide chemistry can be considered with preference as N-protected amino acid components for oxazolidinone formation within the scope of the invention.

Therefore, in a further method variant preferred in accordance with the invention compounds of formula III in which formula $R^1$ stands for an N-protective group are used for coupling with D-Ala-thietane amide, which compound of formula III is obtained by reacting N-protected L-aspartic acid of general formula IV

in which
$R^1$ stands for boc, Z, TFA, aloc, teoc, formyl, tosyl, fmoc or moc with carbonyl compounds, preferably aldehydes, especially preferably formaldehyde or a precursor producing formaldehyde in the reaction and in which the reaction product from the compound of formula IV with formaldehyde or one of its precursors such as paraformaldehyde or trioxane is used without isolation and purification for coupling with the compound of general formula II.

The compounds of general formula III in which $R^1$ does not stand for H and for which the following is valid
$R^1$=Z, $R^6$, $R^7$=H, (Chem. Pharm. Bull. 1969, 17, 1679);
$R^1$=boc, $R^6$, $R^7$=H (J. Polym. Sci., Polym. Chem. Ed. 1978, 16, 2237);
$R^1$=teoc, $R^6$, $R^7$=H (Bull. Chem. Soc. Jpn. 1982, 55, 633);
$R^1$=fmoc, $R^6$, $R^7$=H (Chimia 1992, 46, 314);
$R^1$=tosyl, $R^6$, $R^7$=H (Chem. Ber. 1962, 95, 1009);
$R^1$=moc, $R^6$, $R^7$=H (THL 1992, 33 2669); and
$R^1$=aloc, $R^6$, $R^7$=H (Synthesis 1991, 935)
are known.

The compounds in which $R^1$ stands for TFA or formyl are novel.

The splitting-off of the N-protective groups in order to obtain the unprotected compound of formula I can take place according to methods known in the literature. They are described e.g. in textbooks like Houben-Weyl, volume 15/1.

According to the invention L-aspartic acid N-protected with boc or formyl is used with particular advantage as compound of formula IV.

The synthesis of the compounds of general formula III and their conversion to compounds of formula I with compounds of formula II is best carried out in analogy with the processing mode for Z-oxazolidinone described in the following. Z-L-Asp is reacted with paraformaldehyde in an organic solvent, preferably toluene or methylisobutylketone, to the corresponding 1,3-oxazolidinone. The latter is then agitated with 1 equiv. of the amine component of general formula II in the presence of an auxiliary base such as e.g. a tert. amine, e.g. triethylamine, at elevated temperature—preferably 60° C. for several hours, preferably 6. The mixture is worked up and the Z coupling product obtained in 85% yield. The splitting-off of the Z group can not take place by means of catalytic hydrogenation since the sulfur present in the molecule inhibits the catalyst. The removal of the protective group therefore takes place in the glacial acetic acid/HBr system. The residue obtained is worked up in accordance with U.S. Pat. No. 4,411,925.

The coupling products of oxazolidinones of general formula III which carry an other of the above-named protective groups, and compounds of general formula II are de-protected according to standard methods.

If the boc- or formyl protective group is used, which are preferred by the invention, the splitting-off accordingly becomes simpler.

The compounds of general formula II are produced according to methods known in the literature (U.S. Pat. No. 4,411,925) within the scope of the method of the invention. The compounds of general formula II are preferably obtained thereby by coupling D-alanine compounds of general formula V

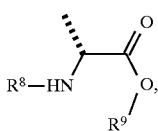

in which $R^8$ is an N-protective group which can be selectively split off and $R^9$ is a group which is known from peptide chemistry and activates the carbonyl group with thietane amines of general formula VI

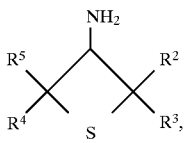

in which $R^2$–$R^5$ have the significance indicated for formula I.

Further details can be gathered from the entire U.S. Pat. No. 4,411,925.

According to the invention the thietane amines of general formula VI are preferably obtained by condensation of thietanones of general formula VII

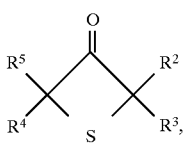

in which $R^2$–$R^5$ have the significance indicated for formula I with amine derivatives of general formula VIII

in which X stands for OH, O-alkyl, O-aryl, O-acyl or $NHR^{10}$ and $R^{10}$=$C_1$–$C_4$-alkyl, aryl, aralkyl, tosyl, mesyl or acyl or their salts such as e.g. hydrohalogenides, phosphates, citrates, acetates or sulfates, to thietane imines of general formula IX

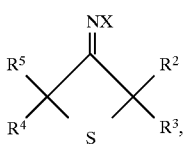

in which $R^2$–$R^5$ have the significance indicated for formula I and X has the significance as in formula VIII, and by subsequent reduction of the thietane imine derivatives obtained.

Reactions for preparing thietane imines of general formula IX ($R^2$–$R^5$=methyl) are described in Chem. Ber. 1991, 124, 1747 (hydrazone: 97% yield, 93 h reaction time) and in Tetrahedron 1986, 42, 5301 (tosylhydrazone: 38% yield, 4 d reaction time).

The corresponding oxime (X=OH, $R^2$–$R^5$=methyl) is synthesized in U.S. Pat. No. 4,692,512 and EP-A 168,112. The reaction instructions indicated in them refer to a procedure from U.S. Pat. No. 4,411,925. However, if the instructions for synthesizing the oxime indicated there are followed, the latter is obtained only in a <30% yield. The oxime obtained is then reduced with a large excess (5 hydride equivalents) of lithium aluminum hydride in only 35% yield to the amine.

Thietanones of general formula VII ($R^2$–$R^5$=methyl) can be reduced to the amine according to U.S. Pat. No. 4,411,925, EP-A 34,876, U.S. Pat. No. 4,399,163, EP-A 69,811, U.S. Pat. No. 4,517,379 with a large excess of ammonium acetate and sodium cyanoboron hydride in 42% yield.

According to U.S. Pat. No. 4,851,548 a Leuckart-Wallach reduction of the thietanone of general formula VII ($R^2$–$R^5$=methyl) likewise succeeds with a large excess of formamide in max. 65% yield.

In general, the reduction of imine derivatives can take place enzymatically or electrochemically by means of heterogeneous catalytic hydrogenation, by boranes, by lithium aluminum hydride, by alkali metals in ammonia, zinc in glacial acetic acid (Houben-Weyl, volume E16d, part 2).

A basic disadvantage of the known methods is the poor yield, which did not permit an economical production of compounds of general formula VI in the past. Thus, the imine derivatives of general formula IX can be prepared according to the state of the art only in poor yields or with extremely long reaction times whereas the known reduction methods deliver poor yields in every instance and require large excesses of the reducing agent or are very difficult to carry out on an industrial scale. Among other things, imine derivatives are preferably reduced on a large scale by means of heterogeneous catalytic hydrogenation. However, this method can not be employed with imines of general formula IX because the sulfur present in the molecule inhibits the catalyst.

As a result of the fact that according to the invention the condensation of the thietanone of general formula VII is carried out with the amine of general formula VII or its salt in an autoclave at a temperature >80° C., preferably >100° C., in the presence of a salt of an acid whose $pK_a$ value is in a range between 4 and 1 and that the following reduction is carried out with sodium boron hydride or lithium boron hydride and an activator, it is possible in an extremely advantageous manner to make available the thietane amines of general formula VI, which were not able to be obtained in the past in a satisfactory yield, in high yields (>90% yield for the condensation reaction relative to the thietanone of general formula VII and also >90% yield for the reduction reaction relative to the thietane imine derivative of general formula IX).

Thus, starting with the particular thietanone, yields of >80% for the corresponding thietane imine result for the method of the invention. This increase, which could not have been readily predicted, is co-causal for the development of an economically interesting method of producing the dipeptide sweeteners of general formula I.

As is known from the state of the art, thietane imine derivatives of general formula IX were previously able to be prepared only in extremely poor yields or with extremely long reaction times.

According to the invention it was now unexpectedly found that thietane imine derivatives of general formula IX can be prepared in very good space/time yields if a closed autoclave is used at a high temperature for their production with the simultaneous addition of a base of a weak acid, preferably an alkali salt of phosphoric acid.

The temperature to be used thereby depends, just as does the addition of the auxiliary base, on the thietanone derivative to be converted.

The temperature should be as high as possible in order that a rapid reaction occurs. On the other hand, byproducts can form at high temperatures, especially if the acidic strength of the acid used is too high. The fact that the $pK_a$ value of the acid used and conjugated to the auxiliary base is between 4 and 1 brings it about that the formation of byproducts is completely suppressed at a sufficiently rapid reaction, in which instance it is obviously possible to avoid a decomposition of the thietane ring. This is surprising and could not have been foreseen.

Within the scope of the invention temperatures of >80° C. are necessary, of >100° C. are preferred and quite particularly high temperatures of 120° C. or higher are advantageous for the condensation reaction between thietanones of general formula VII and amine derivatives of general formula VIII in the closed autoclave. The auxiliary base to be used can potentially be compounds whose conjugated acid has a $pK_a$ value in a range of 4 to 1, preferably monoalkali salts of phosphoric acid, e.g. potassium dihydrogen phosphate. Other salts which can be used with advantage include e.g. sodium formate, sodium citrate. In an especially preferred method variant of the invention an acid addition salt of the amine of general formula VIII can be used with an acid whose $pK_a$ value is between 4 and 1 as base of a weak acid. In this instance a release of the weak acid occurs as the reaction progresses.

According to the invention mixed forms are conceivable, that is, the condensation of the thietanone of general formula VII with an amine of general formula VIII is carried out in the presence of an acid which acid or a mixture of acids, each with a $pK_a$ between 4 and 1, is/are introduced into the reaction via a mixture of auxiliary bases. The mixture of auxiliary bases can be e.g. alkali salts of phosphoric acid with acid addition salts of the amine of general formula VIII. It is understood in this case that a certain stoichiometric amount of the free amine of general formula VIII or one of its salts is also to be used in addition.

The thietane imine derivative obtained in the condensation reaction in accordance with the invention can be reduced within the framework of the invention in a completely surprisingly manner with a readily manageable, activated sodium- or lithium boron hydride, as described in Japanese published, unexamined application Hei-221935 for the reduction of amino acids to amino alcohols, in very good yields (>90%) to the corresponding thietane amine of general formula VI.

Basically, all activators known to the expert in the art can be considered thereby for the reduction step in accordance with the invention. The activators which can be used with advantage include in particular iodine, hydrogen chloride or sulfuric acid. Of these, the use of sulfuric acid or hydrogen chloride as activator for the sodium- or lithium boron hydride is preferred; the use of sulfuric acid for activating sodium boron hydride is especially advantageous.

It is furthermore advantageous for the method of the invention if the reduction reaction is carried out in a solvent. In this connection, solvents with ether structure, optionally in combination with other inert solvents are especially preferred. Dialkyl ethers, cyclic ethers such as THF and dioxane as well as ethylene glycol ethers such as dimethoxyethane, preferably the higher-boiling diethylene glycol dimethyl ether are suitable. Solvents of ethers and other aprotic solvents such as e.g. toluene, etc. are also preferred.

The reaction temperature after the addition of the sulfuric acid must generally be >80%, preferably above 100° C. In a preferred method modification of the invention the reduction step is carried out at 110° C. Low-boiling ethers are therefore used under elevated pressure for the reaction.

The combination of sodium boron hydride with sulfuric acid as activator has proven to be a reduction system which can be used with particular advantage for the reduction step of the invention. This system has the advantage that the reducing and activating agents to be used are readily manageable and relatively economical as well as extremely effective.

The two-stage method of the invention for producing thietane amines of general formula VI from thietanones of general formula VII has proven to be especially advantageous if a compound is used as thietanone of general formula VII in which compound the groups $R^1$–$R^4$ stands for methyl and/or if a compound in which X stands for OH is selected as amine derivative of general formula VIII. In as far as the amine derivatives of general formula VIII are capable of forming salts, it is understood that even these salts can be used in the autoclave for the condensation. Examples for salts are, among others, hydroxylamine hydrochloride or hydroxylamine dihydrosulfate.

Methods for producing the thietanones of general formula VII having significance as intermediate products in the method of the invention are already known from the literature.

Thus, a production variant for a compound of general formula I with $R^1$–$R^4$=methyl is known from Tetrahedron Lett. 1985, 26, 5187 in which variant this compound is produced via a carbene addition to a cyclic disulfide. However, the yields are extremely poor in this variant.

Somewhat better yields are obtained in the production of compounds of general formula VII via a dibromination of ketones of general formula XI

(XI)

and subsequent cyclization with hydrogen sulfide in the presence of a base or with NaHS or Na₂S (Arkiv Kemi 1963, 21, 295; J. Chem. Soc. Perkin Trans I, 1975, 2513, ibid 1976, 2590; J. Am. Chem. Soc. 1976, 98, 6696; Chem. Ber. 1980, 113, 2255; J. Med. Chem. 1990, 33, 1052; Chem. Ber. 1991, 142, 1747; J. Am. Chem. Soc. 1976, 98, 7081; Chem. Ber. 1984, 117, 277; J. Chem. Soc. Perkin Trans I 1984, 2457; Tetrahedron 1986, 42, 5301; U.S. Pat. No. 4,851,548).

However, these known methods have the disadvantage that bromine is used and a bromide compound accumulates as waste product which must be worked up or appropriately disposed of. A further disadvantage can be seen in the use of the very toxic hydrogen sulfide. Both aspects are critical as regards work safety measures and environmental impact.

As a result of the fact that β-oxosulfenyls of general formula X

(X)

in which $R^2$–$R^5$ have the significance indicated for formula I and

Y stands for Cl, Br, I are cyclized within the scope of the invention in an organic solvent under the influence of a base, it became possible in a way which could not have been readily foreseen to distinctly increase the yields indicated in the literature. Furthermore, it was possible in an especially advantageous manner to avoid the use of the generally very toxic hydrogen sulfide, which is otherwise used for the cyclization of the dibromo compound of general formula (b)

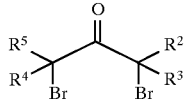
(b)

The cyclization of oxosulfenyl compounds of general formula X can take place thereby in inert organic solvents. The solvents preferred by the invention include e.g. ethers such as e.g. THF, diethyl ether, diisopropyl ether or tertiary butyl ether, ($C_1$–$C_6$) alcohols such as e.g. methanol, ethanol, isopropanol, n-propanol, tert. butanol, n-butanol, n-pentanol or n-hexanol as well as aliphatic or aromatic hydrocarbons such as e.g. n-hexane, cyclohexane or toluene or mixtures of these cited solvents, and alkanes; solvents such as methanol, ethanol, isopropanol, butanol and tetrahydrofuran, diethyl ether, diisopropyl ether, tertiary butylmethyl ether are quite especially preferred within the framework of the invention.

Basically, a large number of substances can be used within the framework of the invention as base for the cyclization reaction. The compounds used with preference include potassium carbonate, sodium hydride as well as alkali alcoholates. The use of KOtBu is quite especially preferred when ethers are used as solvent as well as, when alcohols are used, the use of the corresponding sodium alcoholates.

The beta-oxoxulfenyl compounds of general formula II required for the cyclization to thietanones can be produced in accordance with methods known in the literature. It is known from Helv. Chim. Acta 1966, 49, 2344 and J. Prakt. Chem. 1978, 321, 1017 that diisopropylketone can be reacted with sulfur dichloride to the corresponding oxysulfenyl chloride of formula (a)

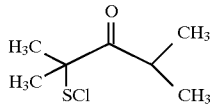
(a)

It is suggested thereby e.g. in Helv. Chim. Acta 1966, 49, 2344 that the reaction between sulfur dichloride and diisopropylketone be carried out by adding sulfur dichloride dropwise to a solution of diisopropylketone in chloroform at 50° to 60° C. with a little aluminum chloride as catalyst. According to the formula indicated in this publication the reaction mixture is distilled in a fractionated manner after the end of the development of hydrogen chloride in order to isolate the reaction products. The oxosulfenyl chloride of formula a is obtained thereby solely in approximately 50% yield.

A further possibility of producing the sulfenyl chlorides of formula a consists of the conversion of diisopropylketone with disulfur dichloride to bisdiisopropyldisulfide (lit.: Helv. Chim. Acta 1966, 49, 2344. Yield: 55%). It is also known that disulfides can be converted with chlorine to the corresponding sulfenyl chlorides (lit.: Houben Weyl "Methoden der organic Chemie" [German—"Methods of Organic Chemistry"], vol. E11, p. 77 ff).

β-oxosulfenyl compounds of formula X can be obtained in an advantageous manner within the framework of the invention by reacting ketones of general formula XI

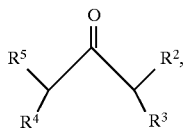
(XI)

in which $R^2$–$R^5$ have the significance indicated for formula I with sulfur compounds of general formula XII $SY_2$   (XII)

in which Y stands for Cl, Br and/or I under exclusion of an addition of solvent and of further Lewis acids.

Furthermore, the β-oxosulfenyl compounds of formula X can be obtained by reacting ketones of general formula XI

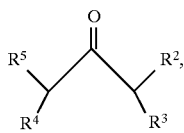
(XI)

in which
$R^2$–$R^5$ have the significance indicated for formula I with compounds of general formula XIII $S_2Y_2$   (XIII)

in which Y stands for Cl, Br and/or I under exclusion of an addition of solvent and further Lewis acids and subsequent reaction with $Y_2$ in which Y has the significance cited above.

In contrast to the methods known from the state of the art the reaction for producing the β-oxosulfenyl compounds of formula X can be carried out therewith within the framework of the invention without solvent and without the addition of a Lewis acid, as a result of which the yields indicated in the literature were able to be significantly increased. Furthermore, the fact is of especially great advantage that the reaction mixture accumulating during the production of the oxosulfenyl compounds of formula II in accordance with the method of the invention can be processed further without further complicated workup simply by dissolution in an organic compound suitable as solvent.

Moreover, it is preferred according to the invention to select sulfur dichloride as compound of general formula XII and disulfur dichloride of general formula XIII and chlorine as $Y_2$ for splitting for the reaction of the ketones of general formula XI. These sulfur compounds can be managed reliably and simply and permit the production of the β-oxosulfenyl compounds of formula X in a high yield which are to be cyclized in accordance with the invention.

The following examples explain the invention:

EXAMPLE 1

Production of 2-(2,4-dimethyl-3-oxo-pentyl)-sulfenyl chloride=compound X with $R^2$–$R^5$=methyl and Y=Cl 428 ml (3 moles) diisopropylketone are placed in a 1l three-neck flask with dropping funnel, thermometer and vacuum connection. 0.25 equivalents sulfur dichloride are now slowly added. After the reaction has started (temperature rise) the remaining 0.75 equivalents sulfur dichloride are added under ice cooling in such a manner that the temperature does not exceed 30° C. After the decrease of the development of hydrogen chloride the mixture is agitated further after 30 min and then the residual hydrogen chloride is removed at 20 mbar in a water jet vacuum. Sulfenyl chloride is obtained with >90% yield.

EXAMPLE 2
Production of 2,2,4,4-tetramethylthietanone=compound VII with $R^2$–$R^5$=methyl 1.8 g (10 mmol) of the sulfenyl chloride obtained in example are dissolved in 140 ml tetrahydrofuran and dripped under ice cooling into a solution of 1.23 g (11 mmol) potassium tertiary butylate in 50 ml tetrahydrofuran. The mixture is agitated approximately 1 hour further. The workup takes place by acidifying with 1M hydrochloric acid to pH=3. After the addition of 50 ml water the solution is extracted 3 times with 100 ml diethyl ether. The collected ether phases are dried over magnesium sulfate. After filtration the yield is determined with HPLC at 91%.

EXAMPLE 3
Production of the thietanone oxime of general formula IX with $R^2$–$R^5$=methyl, X=OH 7.2 g (50 mmol) of the thietanone from example 2 ($R^2$–$R^5$=methyl) are suspended with 6.9 g (100 mmol) hydroxylamine hydrochloride and 6.8 g (50 mmol) potassium dihydrogen phosphate in 200 ml methanol and heated in an autoclave for 12 h to 120° C. Then, 100 ml water are added to the suspension and the methanol removed in a vacuum. The oxime crystallizes out, is filtered off and dried. 7.2 g (90.5%) of the oxime is obtained.

EXAMPLE 4
Production of the thietane amine of general formula VI with $R^2$–$R^5$=methyl 790 mg (5 mmol) of the oxime from example 3 ($R^2$–$R^5$=methyl, X=OH) are dissolved in 200 ml diglyme and compounded with 190 mg (5 mmol) sodium boron hydride. Then, 0.6 ml of a solution of 48 ml diglyme and 12 ml conc. sulfuric acid are added dropwise at −15° C. The mixture is carefully heated to 110° C. and the suspension left at this temperature for approximately 4 h. 10 ml 20% KOH solution are then added and the mixture heated for a further 60 min to 100° C. This solution is used without further workup for further processing. The yield of thietane amine, determined by HPLC, is 90.5% relative to the oxime used in accordance with example 3.

EXAMPLE 5
Production of 2-(2,4-dimethyl-3-oxo-pentyl)-sulfenyl chloride ($R^2$–$R^4$=in formula II=methyl, X=Cl)

4 equiv. DIPK are placed in a 1 l three-neck flask provided with dropping funnel and thermometer as well as a distillation fixture. 1 equiv. $S_2Cl_2$ is added at <10° C. After the reaction is completed excess DIPK is removed in a vacuum and chlorine is then introduced until saturation. The readily volatile compounds are then removed in a vacuum and the sulfenyl chloride can be used in the following reaction.

EXAMPLE 6
Production of 2,2,4,4-tetramethylthietanone ($R^1$–$R^4$ in formula I=methyl)

The sulfenyl chloride of example 5 is dripped into a solution of 1.5 equiv. (relative to the sulfenyl chloride) sodium methylate in methanol. The mixture is then heated 3–4 h on reflux. ⅓ th of the volume water is added in the heat, the mixture allowed to cool off and a filtering off performed. The ketone is obtained in >80% yield as a colorless solid with a camphor-like odor.

EXAMPLE 7
A) Coupling of D-Ala-thietane amide of general formula III with Z-oxazolidinone of general formula III ($R^6$=$R^7$=H, $R^1$=Z group)

26.7 g (100 mmol) N-benzyloxycarbonyl aspartic acid are dissolved with 6.0 g (200 mmol) paraformaldehyde and 0.38 g (2 mmol) p-toluene sulfonic acid in 500 toluene and heated 1 h under reflux at 100° C. on the water separator. The solution is then compounded with 21.6 g (100 mmol) D-Ala-thietane amide of general formula II and 14 ml (100 mmol) triethylamine and heated for 6 h to 60° C. The solution is then washed with 100 ml 1N hydrochloric acid and subsequently with 100 ml water. The org. phase is dried over magnesium sulfate. After filtration the matter is evaporated to low bulk in a vacuum and the Z-protected alitame of general formula I ($R^1$=Z) is obtained in 85% yield.

B) Coupling of the D-Ala-thietane amine of general formula II with oxazolidinone of general formula III ($R^1$=H, $R^{6,7}$=$CF_3$):

13.3 g (100 mmol) L-Asp are suspended in 300 ml DMF. A slight current of hexafluoroacetone is conducted into the suspension. After 2.5 to 3 equiv. have been conducted into the solution the mixture is agitated until everything has gone into solution. The hexafluoroacetone hydrate formed is then removed in a vacuum and trapped in a certain amount of water. The solvent is then removed in a vacuum. The remaining oily remainder is dissolved in 100 ml THF and slowly compounded with a solution of 21.6 g (100 mmol) D-Ala-thietane amide in 100 ml THF at RT. The mixture is agitated 12 h, the developing hexafluoroacetone removed in a vacuum and likewise introduced into a certain amount of water. The aqueous hexafluoroacetone solutions can subsequently be dewatered again with conc. sulfuric acid. The residue remaining after the removal of the solvent is worked up as described in U.S. Pat. No. 4,411,925. Alitame is obtained in 80% yield.

C) Coupling of the D-Ala-thietane amine of general formula II with oxazolidinone of general formula III ($R^1$=H, $R^6$=H, $R^7$=$CCl_3$):

1.33 g (10 mmol) L-Asp are suspended in 3 ml DMSO and compounded with 1.95 ml (20 mmol) chloral. The solution is agitated for 4 h at RT. The solution is then cooled to −15° C. and compounded with 50 ml THF. A solution of 21.6 g (100 mmol) D-Ala-thietane amide in 50 ml THF is allowed to slowly drip at this temperature into the cold mixture. The mixture is agitated 12 h at this temperature, filtering performed and the residue purified by column chromatography. Alitame is obtained in 80% yield.

Further advantages and embodiments of the invention result from the following claims.

We claim:

1. A method of producing L-aspartyl-D-alanine-N-(thietane-3-yl)-amides of the general formula I

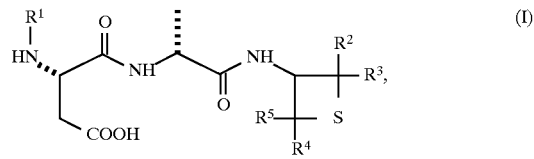

in which $R^1$ stands for H or a protective group capable of being split off and $R^2$–$R^5$ signify independently of each other and equally or differently H or $C_1$–$C_4$ alkyl, linear or branched, by reacting D-alanine-thietane amides of the general formula II

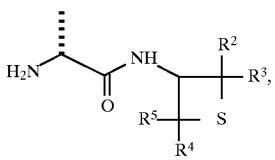

(II)

in which
R²–R⁵ have the significance indicated in formula I with oxazolidinone compounds of the general formula III

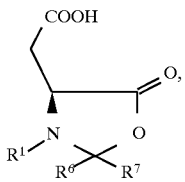

(III)

in which
R¹ has the significance indicated in formula I and
R⁶ and R⁷ stand independently of one another and equally or differently for H, $C_1$–$C_4$ alkyl, linear or branched, $CF_3$, $CCl_3$.

2. The method according to claim 1, characterized in that a compound of formula III with R¹=H, R⁷=$CF_3$ and R⁶=$CF_3$ is used which is obtained by reacting L-aspartic acid with hexafluoroacetone.

3. The method according to claim 2, characterized in that the reaction of L-aspartic acid with hexafluoroacetone is carried out in DMF as solvent and excess hexafluoroacetone and/or hexafluoroacetone hydrate is/are completely recovered.

4. The method according to claim 3, characterized in that the resulting bis-(2,2-trifluoro-4-carboxymethyl)-1,3-oxazolidin-5-one is coupled without further purification with a compound of general formula II.

5. The method according to claim 1, characterized in that a compound of formula III with R¹=H and R⁶ or R⁷=$CCl_3$ is used which is obtained by reacting L-aspartic acid with chloral.

6. The method according to claim 1, characterized in that a compound of formula III is used in which R¹ stands for an N-protective group which compound of formula III is obtained by reacting N-protected L-aspartic acid of general formula IV

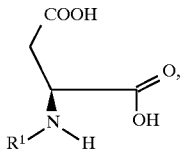

(IV)

in which
R¹ stands for boc, Z, TFA, aloc, teoc, formyl, tosyl, fmoc or moc with carbonyl compounds.

7. The method of claim 6, wherein the carbonyl compound is aldehyde.

8. The method of claim 7, wherein the aldehyde is formaldehyde or a precursor producing formaldehyde in the reaction.

9. The method according to claim 6, characterized in that the reaction product of IV and formaldehyde is used without further isolation and purification for coupling with II.

10. The method according to claim 6, characterized in that the reaction of the N-protected L-aspartic acid is carried out with paraformaldehyde in toluene or MiBK as solvent.

11. The method according to claim 6, characterized in that an L-aspartic acid N-protected with the boc- or formyl group is used.

12. The method according to claim 1, characterized in that the compounds of general formula II are obtained by coupling D-alanine compounds of general formula V

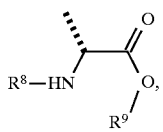

(V)

in which
R⁸ is an N-protective group which can be selectively split off and R⁹ is a group which activates the carbonyl group with thietane amines of general formula VI

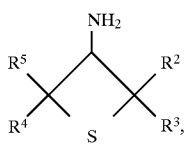

(VI)

in which R²–R⁵ have the significance indicated for formula I.

13. The method according to claim 11, characterized in that the condensation is carried out in an autoclave at a temperature of >80° C., preferably >100° C., in the presence of a salt of an acid whose $pK_a$ value is between 1 and 4 and that the reduction is carried out with sodium- or lithium boron hydride and an activator.

14. The method according to claim 13, characterized in that an acid addition salt of the amine of general formula VIII is used as salt of the acid whose $pK_a$ value is between 1 and 4.

15. The method according to claim 13, characterized in that iodine, hydrogen chloride or sulfuric acid is used as activator in the reduction.

16. The method according to claim 12, characterized in that thietane amines of general formula VI are obtained by condensation of thietanones of general formula VII

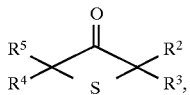

(VII)

in which
R²–R⁵ have the significance indicated for formula I with amine derivatives of general formula VIII

$NH_2$—X (VIII)

in which X stands for OH, O-alkyl, O-aryl, O-acyl or $NHR^{10}$ and $R^{10}$=$C_1$–$C_4$-alkyl, aryl, aralkyl, tosyl, mesyl or acyl or their salts such as e.g. hydrohalogenides, phosphates, citrates, acetates or sulfates, to thietane imines of general formula IX

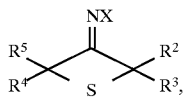

(IX)

in which R²–R⁵ have the significance indicated for formula I and X has the significance as in formula VIII, and by subsequent reduction of the thietane imine derivatives obtained.

17. The method according to claim 16, characterized in that the reduction is carried out in a solvent with ether structure.

18. The method according to claim 16, characterized in that the reduction is carried out at temperatures >80° C., preferably >110° C.

19. The method according to one of claim 16, characterized in that the reduction is carried out with the system sodium boron hydride/sulfuric acid.

20. The method according to claim 16, characterized in that hydroxylamine, its hydrochloride or -sulfate or -phosphate or dihydrosulfate is used for the condensation.

21. The method according to claim 16, characterized in that compounds are reacted in which $R^2$–$R^5$ are each methyl.

22. The method according to claim 16, characterized in that the thietanones of general formula VII are obtained by cyclizing β-oxosulfenyls of general formula X

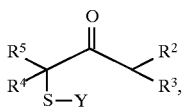 (X)

in which
$R^2$–$R^5$ have the significance indicated for formula I and Y stands for Cl, Br, I in an organic solvent under the influence of a base.

23. The method according to claim 22, characterized in that an ether is used as organic solvent and potassium tertiary butylate as base.

24. The method according to claim 22, characterized in that A ($C_1$–$C_6$) alcohol is used as solvent and the corresponding alkali alcoholate as base.

25. The method according to claim 24, characterized in that methanol is used as solvent and sodium methanolate as base.

26. The method according to claim 22, characterized in that the β-oxosulfenyl compounds of formula X are obtained by reacting ketones of general formula XI

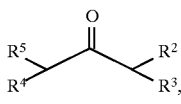 (XI)

in which
$R^2$–$R^5$ have the significance indicated for formula I with compounds of general formula XII $$SY_2 \quad (XII)$$

in which Y stands for Cl, Br and/or I under exclusion of an addition of solvent and of further Lewis acids.

27. The method according to claim 20, characterized in that the β-oxosulfenyl compounds of formula X are obtained by reacting ketones of general formula XI

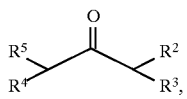 (XI)

in which
$R^2$–$R^5$ have the significance indicated for formula I with compounds of general formula XIII $$S_2Y_2 \quad (XIII)$$

in which Y stands for Cl, Br and/or I under exclusion of an addition of solvent and of further Lewis acids and subsequent reaction with $$Y_2$$

in which Y has the significance cited above.

28. The method according to one of claims 26 or 27, characterized in that the resulting β-oxosulfenyl compounds of formula X are dissolved without workup in an ether and cyclized with a base under obtention of the thietanones according to formula VII.

29. The method according to one of claims 26 or 27, characterized in that compounds are reacted in which the groups $R^2$–$R^5$ all stand for a methyl group.

30. The method according to one of claims 22–27, characterized in that compounds are reacted in which Y stands for Cl.

* * * * *